US012021536B2

(12) United States Patent
Loinaz

(10) Patent No.: US 12,021,536 B2
(45) Date of Patent: Jun. 25, 2024

(54) POSITRON EMISSION TOMOGRAPHY SYSTEM WITH A TIME SYNCHRONIZED NETWORK

(71) Applicant: Marc Loinaz, Los Altos Hills, CA (US)

(72) Inventor: Marc Loinaz, Los Altos Hills, CA (US)

(73) Assignee: Anacapa Semiconductor, Inc., Los Altos, CA (US)

(*) Notice: Subject to any disclaimer, the term of this patent is extended or adjusted under 35 U.S.C. 154(b) by 0 days.

(21) Appl. No.: 17/942,077

(22) Filed: Sep. 9, 2022

(65) Prior Publication Data
US 2023/0006677 A1    Jan. 5, 2023

Related U.S. Application Data

(62) Division of application No. 16/265,400, filed on Feb. 1, 2019, now abandoned.
(Continued)

(51) Int. Cl.
H03L 7/06       (2006.01)
G01N 15/14      (2006.01)
(Continued)

(52) U.S. Cl.
CPC .......... H03L 7/06 (2013.01); G01N 15/1429 (2013.01); G01N 15/1459 (2013.01);
(Continued)

(58) Field of Classification Search
CPC .. H03L 7/06; G01N 15/1429; G01N 15/1459; G01N 2015/1006; G01S 7/4865;
(Continued)

(56) References Cited

U.S. PATENT DOCUMENTS

2005/0113667 A1* 5/2005 Schlyer ................ G01T 1/2985
                                                  250/363.05
2017/0014096 A1* 1/2017 Bouhnik .............. A61B 6/5205
(Continued)

OTHER PUBLICATIONS

Aliaga et al., "PET system synchronization and timing resolution using high-speed data links", IEEE Transactions on Nuclear Science, vol. 58. No. 4, pp. 1596-1605. (Year: 2011).*

Primary Examiner — Kiho Kim
(74) Attorney, Agent, or Firm — Law Office of John Stattler

(57) ABSTRACT

A sensor network, which includes a sensor controller serially coupled to a plurality of sensor modules, is configured to program the sensor modules so as to transfer measurement data to the sensor controller and to synchronize the sensor modules to picosecond accuracy via on-chip or on-module custom circuits and a physical layer protocol. The sensor network has applications for use in PET, LiDAR or FLIM applications. Synchronization, within picosecond accuracy, is achieved through use of a picosecond time digitization circuit. Specifically, the picosecond time digitization circuit is used to measure on-chip delays with high accuracy and precision. The delay measurements are directly comparable between separate chips even with voltage and temperature variations between chips.

13 Claims, 14 Drawing Sheets

Related U.S. Application Data

(60) Provisional application No. 62/625,299, filed on Feb. 1, 2018.

(51) Int. Cl.
| | |
|---|---|
| *G01N 15/1429* | (2024.01) |
| *G01S 7/4865* | (2020.01) |
| *G01S 17/26* | (2020.01) |
| *G01S 17/88* | (2006.01) |
| *G01T 1/29* | (2006.01) |
| *A61B 6/00* | (2006.01) |
| *G01N 15/10* | (2006.01) |

(52) U.S. Cl.
CPC ............ *G01S 7/4865* (2013.01); *G01S 17/26* (2020.01); *G01S 17/88* (2013.01); *G01T 1/2985* (2013.01); *A61B 6/4417* (2013.01); *G01N 2015/1006* (2013.01)

(58) Field of Classification Search
CPC ....... G01S 17/26; G01S 17/88; G01T 1/2985; A61B 6/4417; A61B 6/037; A61B 6/4258
See application file for complete search history.

(56) References Cited

U.S. PATENT DOCUMENTS

2017/0164911 A1\* 6/2017 Lv ..................... G01T 1/2985
2017/0285182 A1\* 10/2017 Fu ..................... G01T 1/2985

\* cited by examiner

US 12,021,536 B2

POSITRON EMISSION TOMOGRAPHY SYSTEM WITH A TIME SYNCHRONIZED NETWORK

RELATED APPLICATIONS

This application claims priority, under 35 U.S.C. § 119(e), to U.S. Provisional Application No. 62/625,299, entitled "APPLICATIONS FOR A TIME COHERENT NETWORK FOR PRECISION SENSING", inventor Marc Loinaz, filed Feb. 1, 2018, and claims priority, under 35 U.S.C. § 120, to U.S. patent application Ser. No. 16/265,400, entitled "APPLICATIONS FOR A TIME COHERENT NETWORK FOR PRECISION SENSING", inventor Marc Loinaz, filed Feb. 1, 2019, both which are expressly incorporated herein by reference.

BACKGROUND

Precision time delay measurement is a requirement for emerging sensor applications. In Positron Emission Tomography (PET) and Light Detection and Ranging (LiDAR), precise measurement of photon time-of-flight (ToF) allows precise quantification of the spatial location of an event. In Fluorescence Lifetime Imaging (FLIM) photon arrival times at a sensor are used to detect the presence of fluorophore-tagged molecules within a biological sample.

In PET, the event of interest is the annihilation of a positron (from a radioactive dye) and an electron within a chemically active region within the body of a medical patient or live laboratory subject. The event produces two gamma ray photons that are travelling in opposite directions. The ToF measurements to a three-dimensional sensor array in a PET scanner allow precise location of the event, which could, for example, indicate the presence of a tumor.

In LiDAR, the event of interest is scattering of photons from a laser pulse. The ToF of laser photons from when they are emitted by the laser, scattered from a target object and then detected in a sensor allows the distance of the target object from the LiDAR system to be precisely resolved. This has applications in Unmanned Autonomous Vehicles (UAVs) and Advanced Driver Assistance Systems (ADAS).

In Fluorescence Lifetime Imaging (FLIM), the event of interest is the generation of fluorescence photons by a laser pulse. The photon arrival times relative to the laser pulse are used to build a histogram of the fluorescence decay transient of a laser-excited molecule. The measurement of the decay time allows detection of fluorophore-tagged molecules within a tissue sample. Additionally, the use of FLIM allows detection of Förster Resonance Energy Transfer (FRET), which allows the measurement of the distance between specific molecules within a cell.

In all of these applications there is a need for more sensors so as to improve system sensitivity (by increasing the number of photons captured) and accuracy as well as to increase measurement throughput. This requires large numbers of sensor chips and sensor modules distributed in arbitrary physical configurations. Furthermore, these sensor systems need to be synchronized to accuracies of picoseconds. To highlight the required timing accuracies, measurement of ToF to within 3.3 ps allows spatial resolution of 1 mm. Current distributed timing synchronization methods do not allow picosecond time measurement accuracy or are difficult to implement and require extensive calibration.

In current sensor systems, time synchronization involves a passive approach as shown in FIG. 1. Since the trace lengths and transmission lines from the reference oscillator all the way to sensor chips 1, 2 and 3 are matched and the clock buffers are assumed to be identical then there will be minimal time skew between the clock signals seen at each chip. In addition, a master reset signal is distributed to the sensor chips using matched-length traces. This allows the state of each chip (including the states of on-chip clock dividers) to be simultaneously initialized so as to be identical across chips.

There are many practical problems with the passive synchronization approach. The clock buffers, while they are nominally identical, may have mismatch due to manufacturing variations. Adding another sensor chip to the system is difficult since it requires redesign of the reference clock distribution circuit to a) add another clock buffer and b) add another clock transmission line that is matched to the others. If there is a mismatch between the temperatures or power supply voltages seen by the sensor chips then there will be mismatches in the on-chip gate delays seen on the chips, which will tend to de-synchronize the chips. The master reset is also problematic since each sensor chip could have some random mismatch. As a result the chips may not be reliably reset to the same state. Therefore, an active synchronization strategy is required that adjusts for 1) slight trace mismatch and chip-to-chip mismatch; 2) voltage and temperature variations between chips; and 3) the possibility of reset state mismatch between chips. Therefore, better solutions for time synchronization are required to meet timing that demand accuracies within picoseconds.

BRIEF DESCRIPTION OF THE DRAWINGS

The novel features of the invention are set forth in the appended claims. However, for purpose of explanation, several embodiments of the invention are set forth in the following figures.

DETAILED DESCRIPTION

Today, there exists networking protocols that allow for the time synchronization of local area network (LAN) elements such as routers, switches and network interface cards within computers, test instrumentation or factory machines. Precision Time Protocol (PTP) is designed to be compatible with Ethernet, the dominant LAN technology in use today. PTP is designed for sub-microsecond time accuracy. White Rabbit (WR) is based on PTP and Synchronous Ethernet and is designed for sub-nanosecond accuracy. White Rabbit was designed for the instrument synchronization, control and data transfers required for large-scale particle physics experiments (e.g. the LHC experiment at CERN).

Both PTP and WR involve the use of network elements that have time stamping capability. The time at which an Ethernet frame is sent or received can be recorded by all compliant network elements. A master-slave hierarchy is specified that allows the master network elements to update the current time at the slave elements. Because master and slave are connected via an electrical cable or fiber optic cable there will be a time delay (or latency) in communication between them. The protocol gives masters the ability to estimate the time delay with which they communicate with their slaves. This allows the masters to pass their local time to the slaves along with the delay information. The slaves then update their local time to the master's time plus the master-to-slave message delay. The result is that the master and slave time readings are nominally identical.

PTP and WR do not give sufficient time synchronization for the aforementioned PET, LiDAR and FLIM applications where time measurement accuracies of picosecond to tens of picoseconds are required. WR has been shown to achieve hundreds of picoseconds of timing accuracy. It involves a coarse time stamping technology with complex sequence of message passing between master and slave that allows the slave to shift its internal clock in fine phase steps so as to achieve synchronization. WR is designed so as to minimize the need for custom integrated circuits designed specifically for the synchronization process.

To achieve accuracy in the range 1-100 ps, custom integrated circuits are required to measure time stamps with sub-100 ps accuracy. These circuits must be combined with a physical layer protocol for measuring the latency in the connections between network elements.

Figure 1:
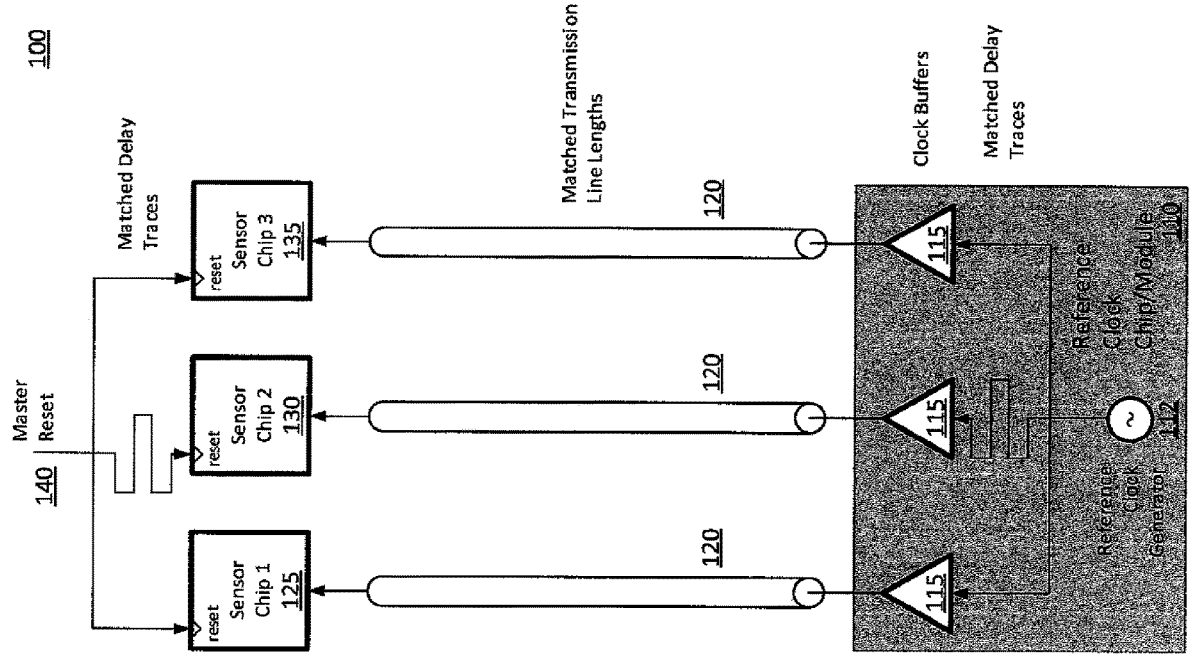
FIG. 1 illustrates a passive approach for time synchronization used in current sensor systems.
Figure 2:
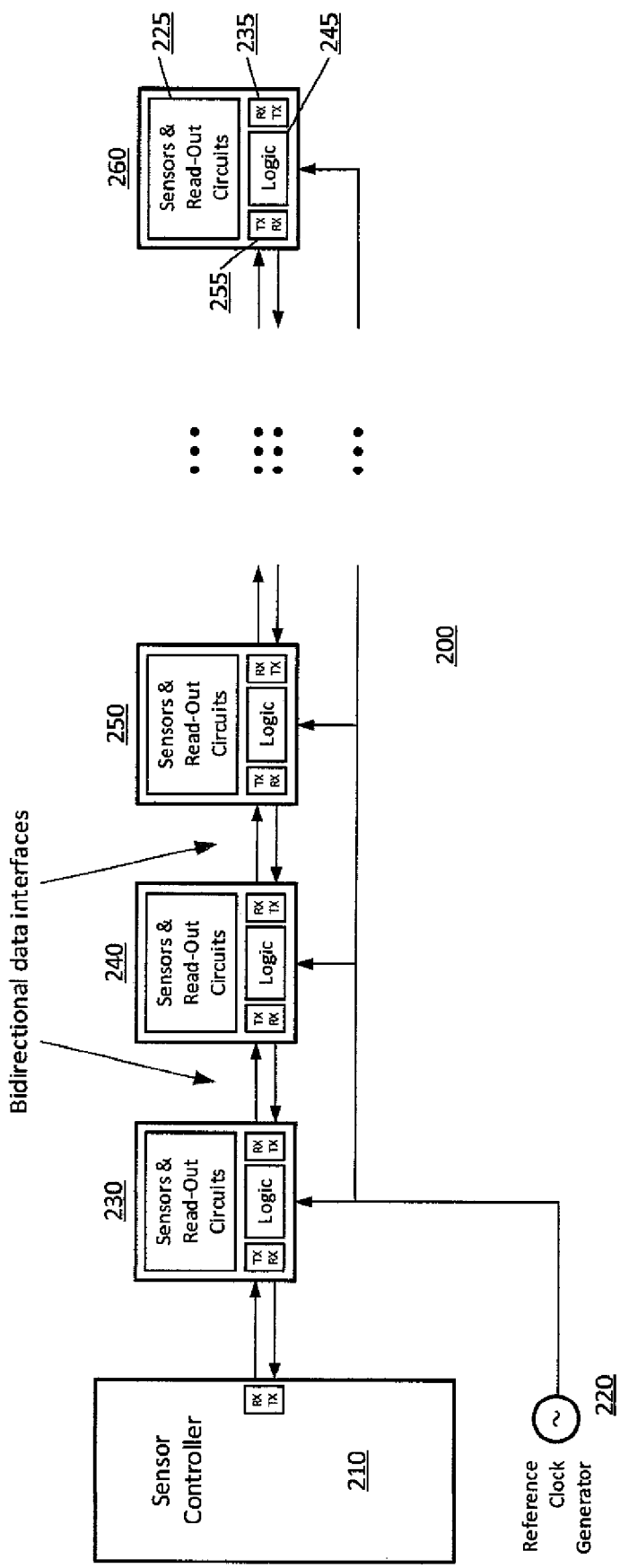
FIG. 2 illustrates one embodiment for a sensor network, including a sensor network for use in PET, LiDAR or FLIM applications.

FIG. 2 illustrates one embodiment for a sensor network, including a sensor network for use in PET, LiDAR or FLIM applications. The sensor network 200 includes a sensor controller (210) serially coupled to a plurality of sensor modules (230, 240, 250 and 260). Each sensor module includes, as shown by example in sensor module 260, sensor and readout circuits (225), logic circuits (245) as well as transceiver circuits (235 and 255). The sensor modules (230, 240, 250 and 260) receive a timing reference from reference clock generator (220). Each sensor module (230, 240, 250 and 260) may be a single chip or a module made out of multiple chips. The network elements (sensor controller (210) and sensor modules (230, 240, 250 and 260) are daisy-chained. This allows straightforward expandability for each chain. The sensor controller (210) may also be designed to service multiple daisy chains. Note that the reference clock (220) is distributed to each network element without any timing skew requirements.

The sensor network (200) allow the sensor controller (210) to a) configure and program the sensor modules (230, 240, 250 and 260), b) the sensor modules (230, 240, 250 and 260) to transfer measurement data to the sensor controller (210), and c) synchronize all the sensor modules (230, 240, 250 and 260) to picosecond accuracy via on-chip or on-module custom circuits and a physical layer protocol.

Figure 3:
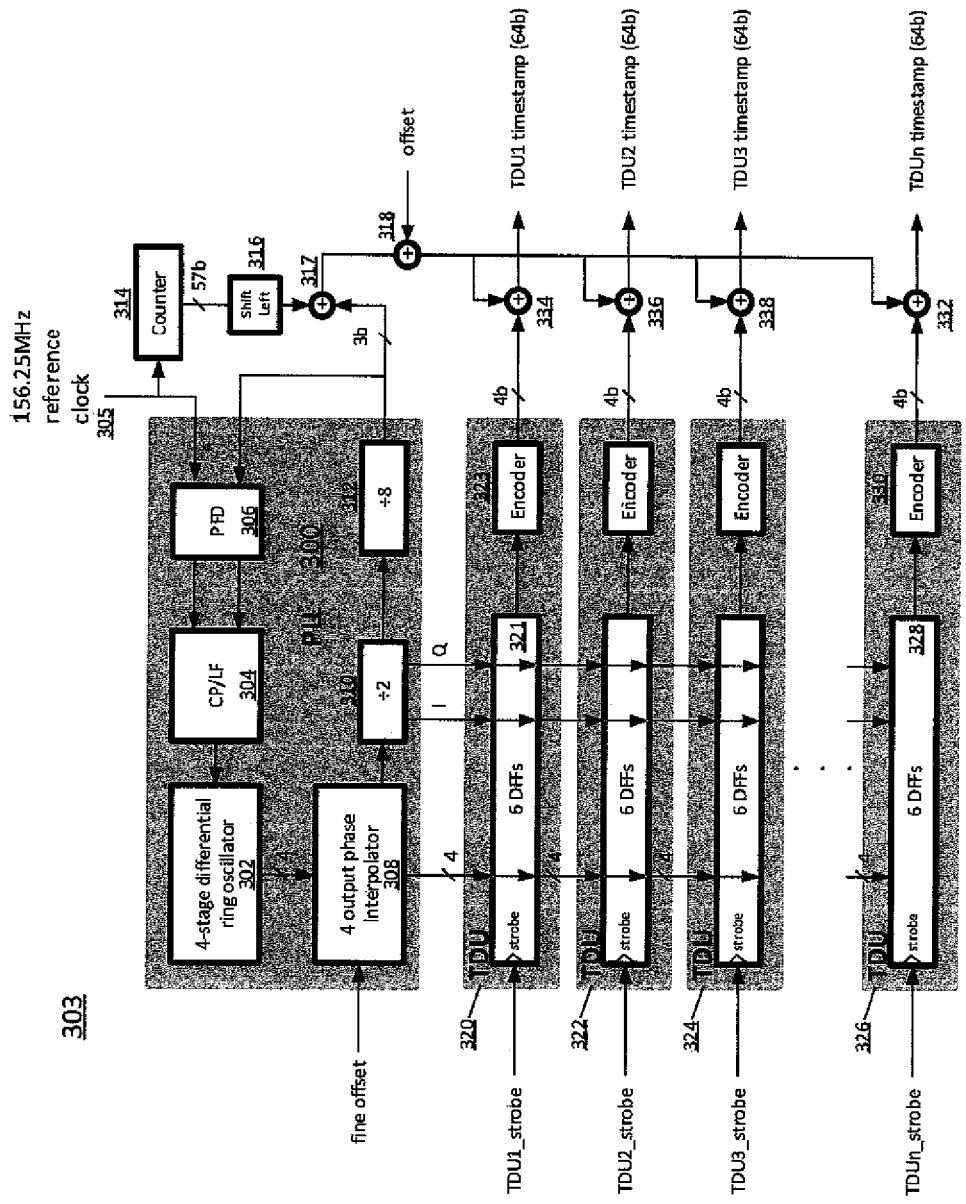
FIG. 3 illustrates one embodiment for a picosecond time digitization circuit.

FIG. 3 illustrates one embodiment for a picosecond time digitization circuit. Circuit 303 may be used to measure on-chip delays with high accuracy and precision. The delay measurements are directly comparable between separate chips even with voltage and temperature variations between chips because the time delay measurement unit is fixed using an on-chip Phase-Locked Loop (PLL).

A PLL (300) consists of a 4-stage ring oscillator (implemented using differential circuits) (302), a phase interpolator (308), divider circuits (310 and 312), a phase-frequency detector (PFD) (306), a charge pump (CP) and loop filter (LF) (304) is phase-locked to the system reference clock (305). With the reference clock (305) at 156.25 MHz and the dividers (310 and 312), as shown in FIG. 3, the VCO (302) will oscillate at 2.5 GHz, and each ring oscillator gate delay will be 50 ps over expected chip supply voltage and temperature variations. This 50 ps unit gate delay forms the least significant bit (LSB) of the time stamping circuit. The 4 ring oscillator stage (302) outputs and the two (in-phase and quadrature) outputs of the divide-by-2 circuit (310) are distributed to each Time Digitization Unit (TDU) (320, 322, 324 and 326). In some embodiments, each TDU (320, 322, 324 and 326) consists of 6 flip-flops and an encoder, such as flip-flops 321 and encoder 323 in TDU 320, that produces a binary representation of the time measurement. The binary output of the encoder for TDUs (320, 322, 324 and 326) represents the occurrence time of the TDU strobe rising edge within the 800-ps clock period of the signal at the input to the divide-by-8 block (312). The three bits of the divide-by-8 binary counter (312) are added to the outputs of a counter clocked by the reference clock (305). This sum is added to the output of each TDU (320, 322, 324 and 326) so as to produce a 64-b representation of the time on the chip. Note that a 64b representation allows time to be recorded with 50 ps precision over a period of 29 years for the circuit in before the time count rolls over.

Note that each TDU (320, 322, 324 and 326) samples the in-phase and quadrature outputs of the divide-by-2 circuit (310). This allows the correct divider state to be sampled while correcting for non-zero divider delay. The correct divider output is chosen based on the sampled state of the ring oscillator stage that clocks the divider.

The time stamping circuit further includes counter 314, shift left 316, summing circuits (317, 318, 334, 336, 338 and 332). These circuits (314, 316, 317, 318, 334, 336, 338 and 332) allow a global time offset to be injected into the 64-b time representation so as to correct the local chip time relative to a master time with a precision of one TDU LSB. The phase interpolator (308) allows the 4 VCO (302) output signals to be shifted together in sub-LSB steps. This allows for fine time control that would allow chip-to-chip synchronization to less than one LSB.

An arbitrary number of TDUs can be used on a chip. However, it is important that the propagation delays of the 6 clock signals from the PLL be the same for all TDUs. This can be achieved by trace matching and repeater delay matching methods that are part of the known art in custom integrated circuit design.

Note that the LSB precision of the time stamping circuit can be improved by running the ring oscillator (302) faster (by dissipating additional power) or by implementing the circuit (303) in a more advanced process technology. In addition, interpolation between ring oscillator (302) stages can be used to reduce the LSB size further. An LSB of <10 ps should be readily achievable with commercially-available 16 nm finFET CMOS processes.

Synchronization is performed via a master-slave algorithm where, for two chips next to each other on the daisy chain, the chip electrically closer to the controller is the master and the chip farther from the controller is the slave. The master causes the slave to update its internal time to match that of the master.

The sensor network (200, FIG. 2) may be designed to use on Ethernet-like protocol to pass data between master and slave. In this case, data frames would be transmitted between chips with the frames interspersed with idle characters. It is during the idle periods that synchronization steps may be performed. Alternatively, regularly scheduled synchronization periods could be defined. While synchronization could be done at system start-up, it is important that synchronization occurs regularly even after system start-up in order for the system to correct for temperature and power supply voltage changes that occur after start-up.

Figure 4:
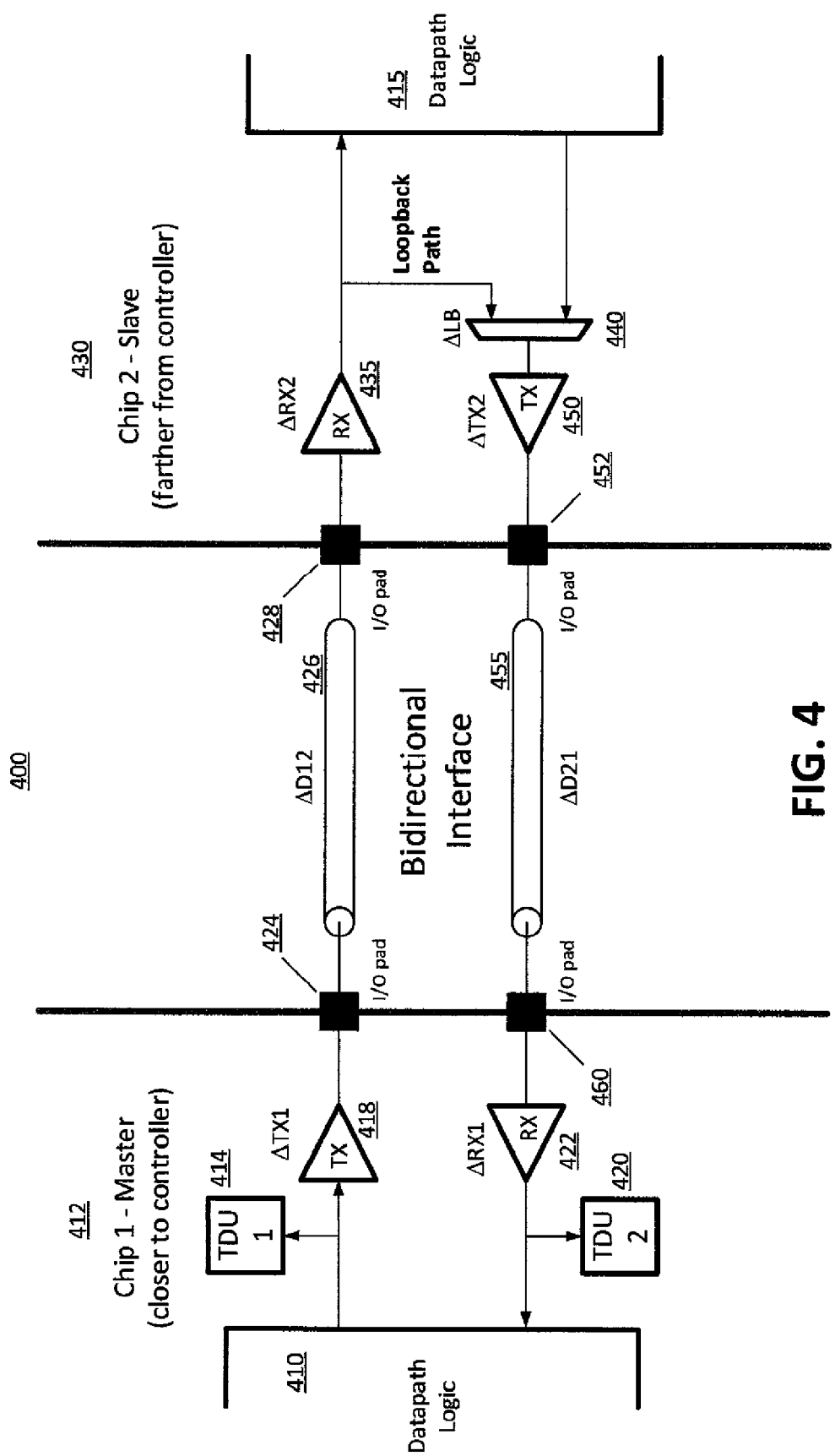
FIG. 4 illustrates embodiments for time synchronization across master and slave devices.

FIG. 4 illustrates one embodiment for synchronization between a master IC (412) and a slave IC (430). For this embodiment, the master IC (412) and slave IC (430) include datapath logic (410 and 415), TDUs (414 and 420), and transceiver circuits (418, 422) and (435, 440 and 450). Synchronization occurs with the slave placed in a loopback mode where data received from the master is immediately transmitted by the slave back to the master over bidirectional interface (426 and 455), as shown in FIG. 4.

The master can measure the round drip delay using its on-chip TDUs (414 and 420). The round trip delay can be expressed as:

$$T_{round}=DTX1+DD12+DRX2+DLB+DTX2+DD21+DRX1$$

DTX1 represents the delay through the transmitter (418) (which may include the serializer) on master IC (412). DRX1 represents the delay through the receiver (435) (which may include the deserializer). DTX2 and DRX2 represent transmitter (450) and receiver (435) delays on slave IC (430). DLB represents the delay through the loopback path (440) on slave IC (430). DD12 represents the propagation delay in the interconnect (426) carrying data from master IC 412 to slave IC 430. DD21 represents the propagation delay in the interconnect (455) carrying data from slave IC 430 to master IC (412). Note that the interconnects (426 and 455) may be a printed circuit board traces, electrical cables, or fiber optic cables.

The desired quantity is the latency from master to slave:

$$T_{latency}=DTX1+DD12+DRX2$$

Once $T_{latency}$ is known by the master IC (412), then it can send its own internal time reading to the slave IC (430) along with the value of $T_{latency}$. The slave IC (430) then updates its internal time to master's time plus the $T_{latency}$. If the link is completely symmetrical and DLB is zero then the latency could be determined by simply halving the $T_{round}$ measurement value. In practice this is unrealistic because of implementation details associated with the serializer/deserializer (SerDes) circuits used to realize modern high-speed data networks. The delay through a SerDes TX and RX can vary by multiple bit intervals with the initialization state of the serializer and deserializer subcircuits. Such circuits always include dividers, which will initialize in non-deterministic states. Therefore the delay through a serializer or deserializer is not known unless it is specifically reset. In addition, because of chip-to-chip power supply and temperature variations, there is no guarantee that DTX1 will be the same as DTX2 and that DRX1 will be the same as DRX2. Finally, DLB will not be zero.

Figure 5:
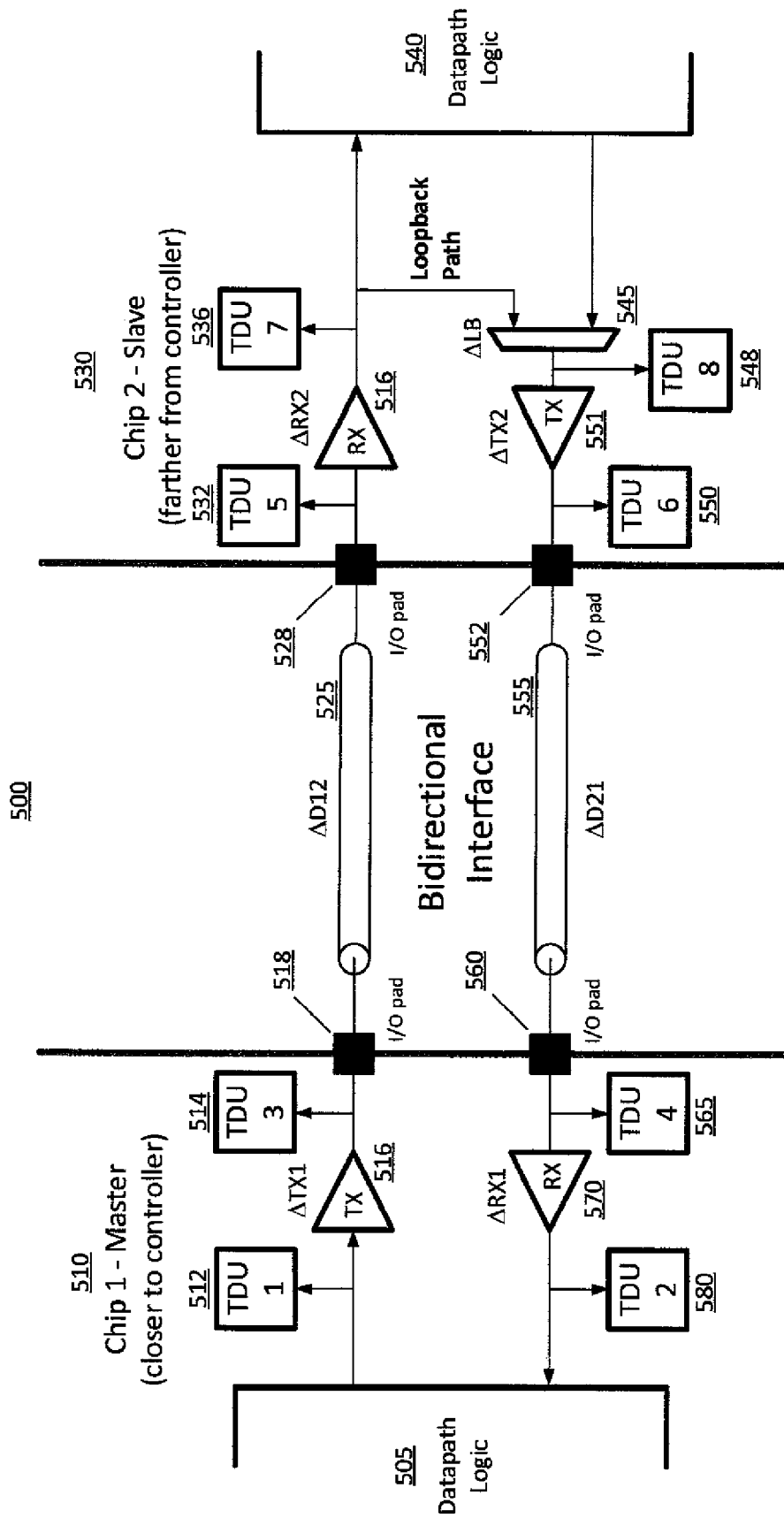
FIG. 5 illustrates embodiments for time synchronization across master and slave devices.

FIG. 5 depicts more precise measurements achieved from the round trip delay components. For this embodiment, the master IC (510) and slave IC (530) include datapath logic (505 and 540), TDUs (512, 514, 532, 536, 548, 550, 565, 580), and transceiver circuits (516, 570) and (534 and 551). With the use of multiple TDUs (512, 514, 532, 536, 548, 550, 565, 580), the delays of various circuits are directly measured. The delay measurements made entirely on one chip are compared to measurements on another chip because of the LSB of the time stamping circuits is the same over all the chips. However, absolute time readings cannot be combined between chips because the internal time is not synchronized between the two chips before the synchronization process is completed.

Using the on-chip TDUs (512, 514, 532, 536, 548, 550, 565, 580), DTX1, DRX1, DTX2, DRX2 and DLB can be measured. By passing data back and forth between the master IC (510) and the slave IC (530), the value of DD12+DD21 can be determined by the master IC (510). Assuming the two passive interconnect (525 and 555) delays are equal, then the master-to-slave latency $T_{latency}$ can be determined using equation (2). For a bidirectional interface (525 and 555) made from matched printed circuit board (PCB) traces, it is a good assumption that DD12 and DD21 are equal. If fiber optic cables are used for the bidirectional interface (525 and 555), then the delay asymmetry can be characterized over temperature and cable length and used to correct the value of DD12.

Note that synchronization between network elements, connected via electrical traces on a PCB, electrical cables or fiber optic cables, is disclosed herein. However, these embodiments may be extended to wireless connections between network elements, such as RF links and free-space optics.

Applications for the Invention

Figure 6:
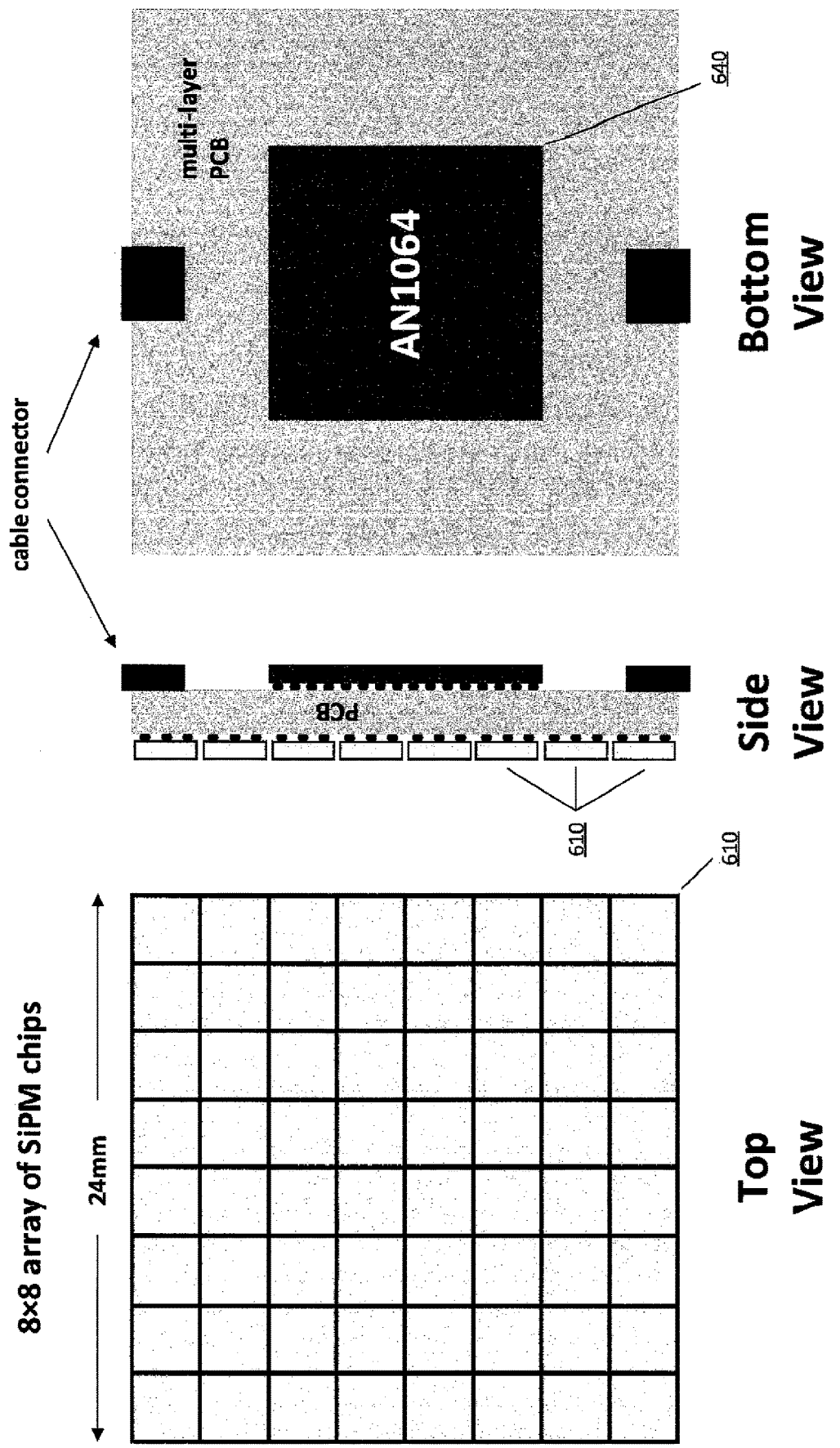

In some embodiments, the circuitry described above for performing time synchronization are integrated onto a silicon chip. FIG. 6 illustrates a configuration for performing time synchronization among sensors, incorporated onto a printed circuit board (PCB) module. Alternatively, the synchronization circuitry can be integrated with a sensor array on a single chip.

For the embodiment shown in FIG. 6, the AN1064 (640) is a readout chip for an array of silicon photomultiplier (SiPMT) sensors (610). Each sensor, with the array of sensors (610), is a highly-sensitive detector of incident photons in the visible to near-infrared spectrum.

Figure 7:
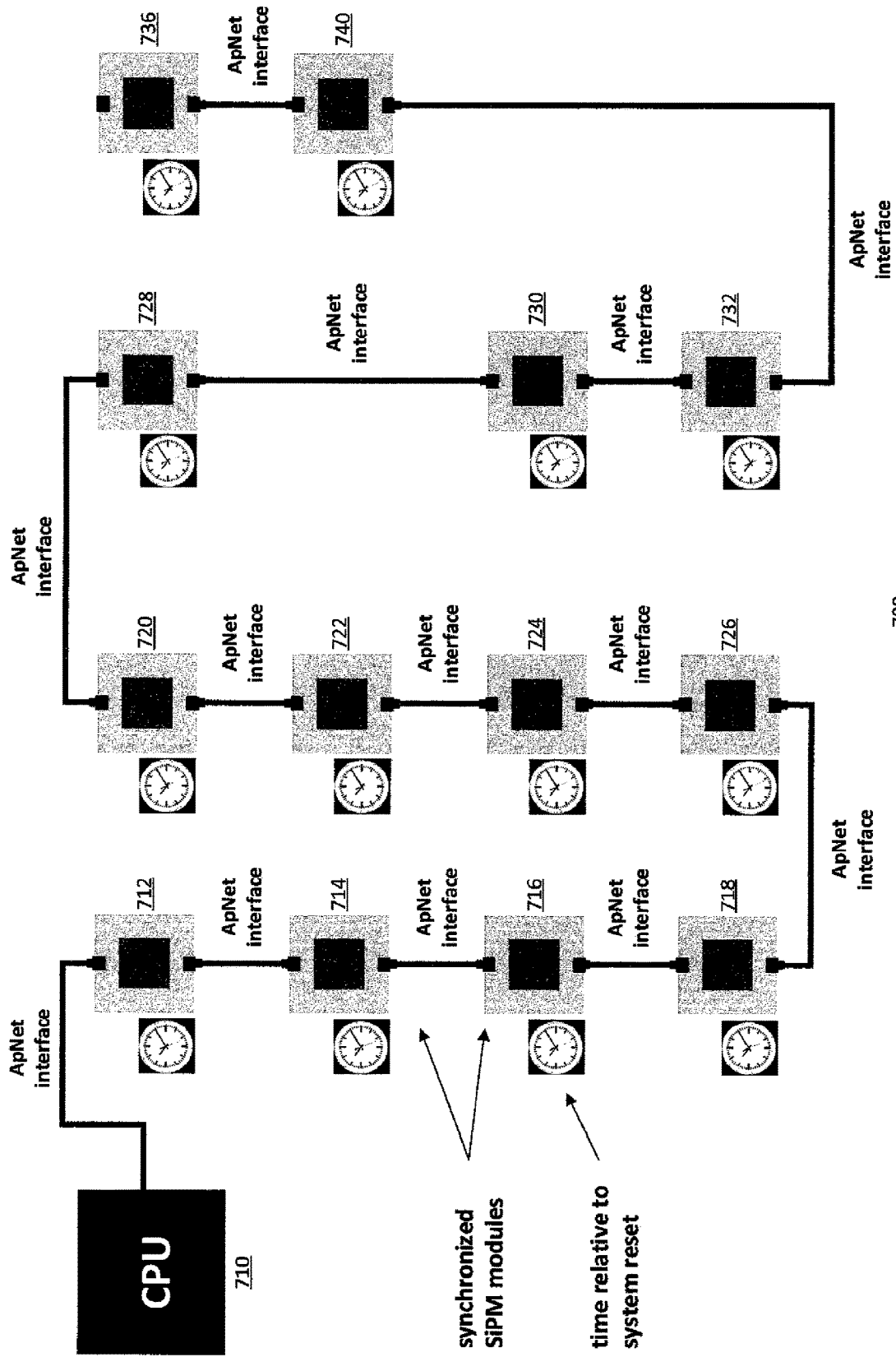
FIG. 7 illustrates a network of sensor modules configured to produce a time synchronized sensor network.

FIG. 7 illustrates a network of sensor modules configured as a time synchronized sensor network. The exemplary network 700 includes a CPU 710, serially coupled to a plurality of modules (712, 714, 716, 718, 720, 722, 724, 726, 728, 730, 732, 736 and 740) via an ApNet Interface. Each module (712, 714, 716, 718, 720, 722, 724, 726, 728, 730, 732, 736 and 740) is synchronized so that the time readings on each module are synchronized to picosecond accuracy using the techniques described herein.

For purposes of nomenclature, "ApNet" refers to the name for the network protocol that connects the sensor modules together. ApNet provides a means for transmitting data from module to module, for programming the modules, for transmitting sensor readout data from each chip to the CPU (710), and for performing time synchronization of each chip in the network using the principles of the invention described herein.

Figure 8:
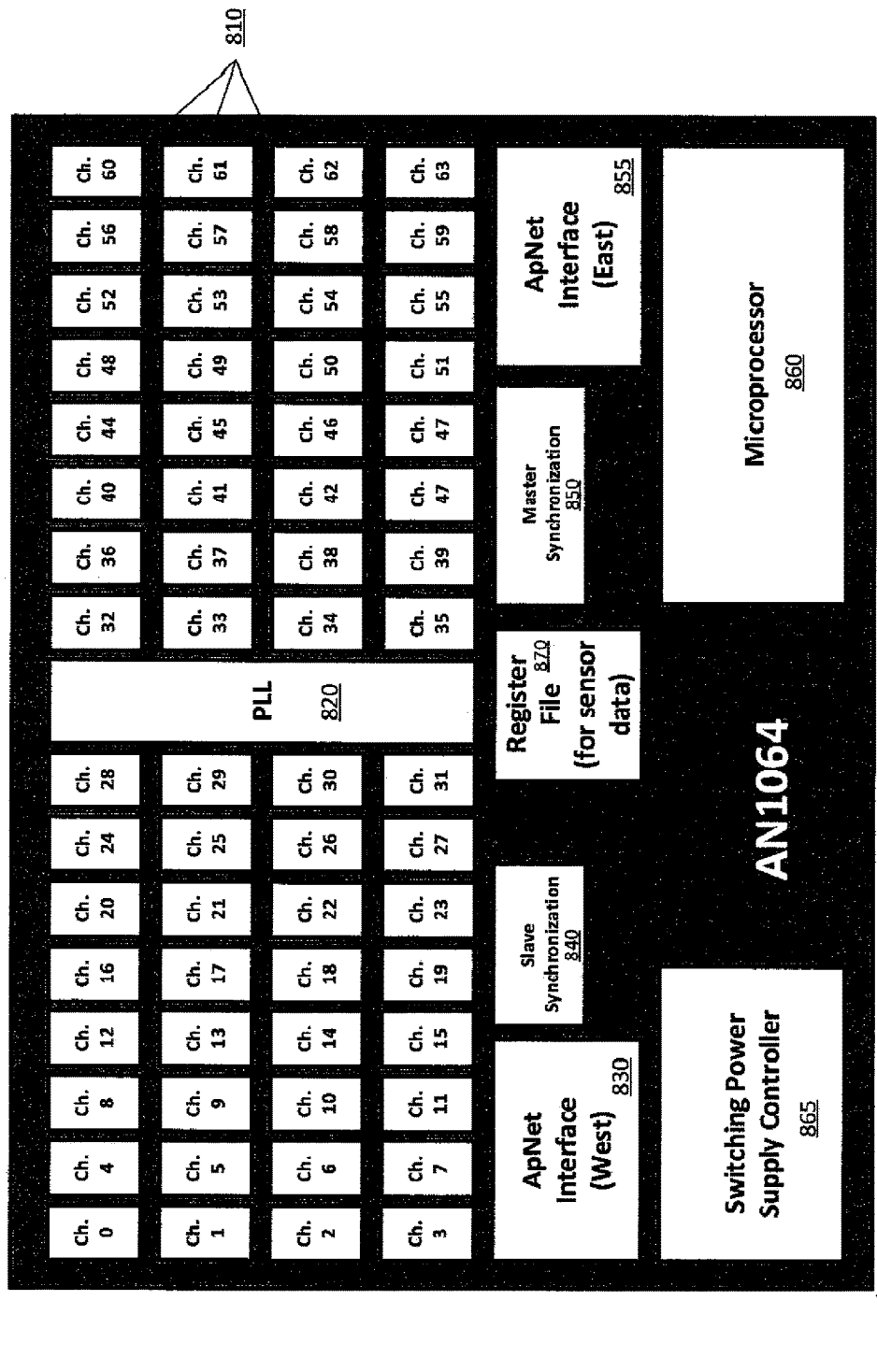
FIG. 8 is a block diagram illustrating one embodiment for the AN1064 chip.

FIG. 8 is a block diagram illustrating one embodiment for the AN1064 chip. For this embodiment, the AN1064 chip (800) consists of readout circuits for each sensor in the SiPMT array (810) (Channels 0 to 63). A register file (870) stores sensor data. A central PLL (820) provides reference clocks for TDUs (not shown) integrated into each readout channel (810) as well as the TDUs used in the synchronization circuits. Circuitry to perform synchronization includes a microcontroller 860, switching power supply controller 865, as well as a slave synchronization block (840) (i.e. a loopback path and TDU circuits) to allow the West interface loopback delay to be measured and conveyed to the link partner on the West interface (830). The master synchronization circuit (850) consists of TDUs and logic that allow measuring the round trip delay for the East interface (855) to its link partner. As the network performs time synchronization, the absolute time on the West interface (830) link partner is passed on to the present chip. This absolute time is then be passed via the East interface (855) to the next chip in the daisy chain.

PET Scanners

Figure 9:
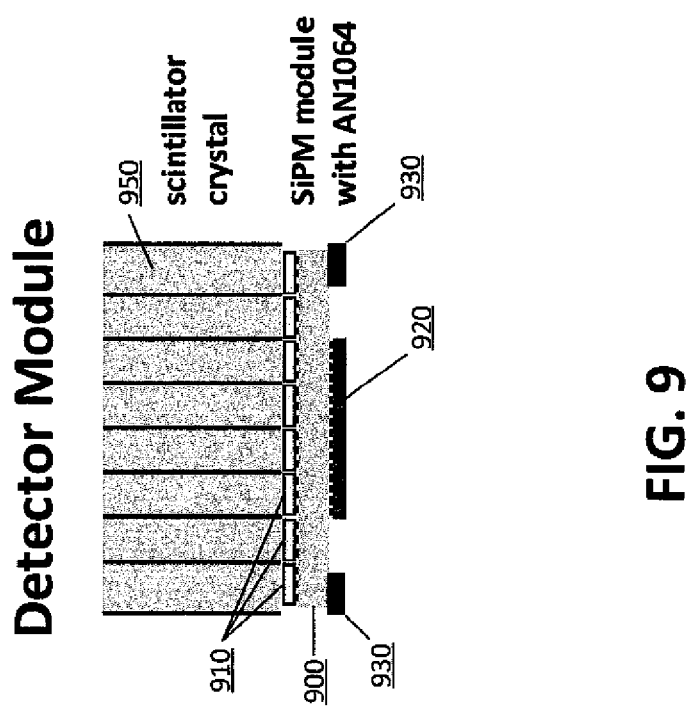
FIG. 9 illustrates one embodiment for a detector module for use in PET applications.

FIG. 9 illustrates one embodiment for a detector module for use in PET applications. For PET applications, each detector module, such as detector module 900, is coupled to a scintillation crystal (950) as shown in FIG. 9. Detector module 900 is configured to allow the gamma rays produced by the positron-electron annihilation event to be converted into visible light sensed by the SiPMT devices (910) on the detector module (900). Synchronization, as described herein, is performed by IC 920 (AN1064) with interface (930).

Figure 10:
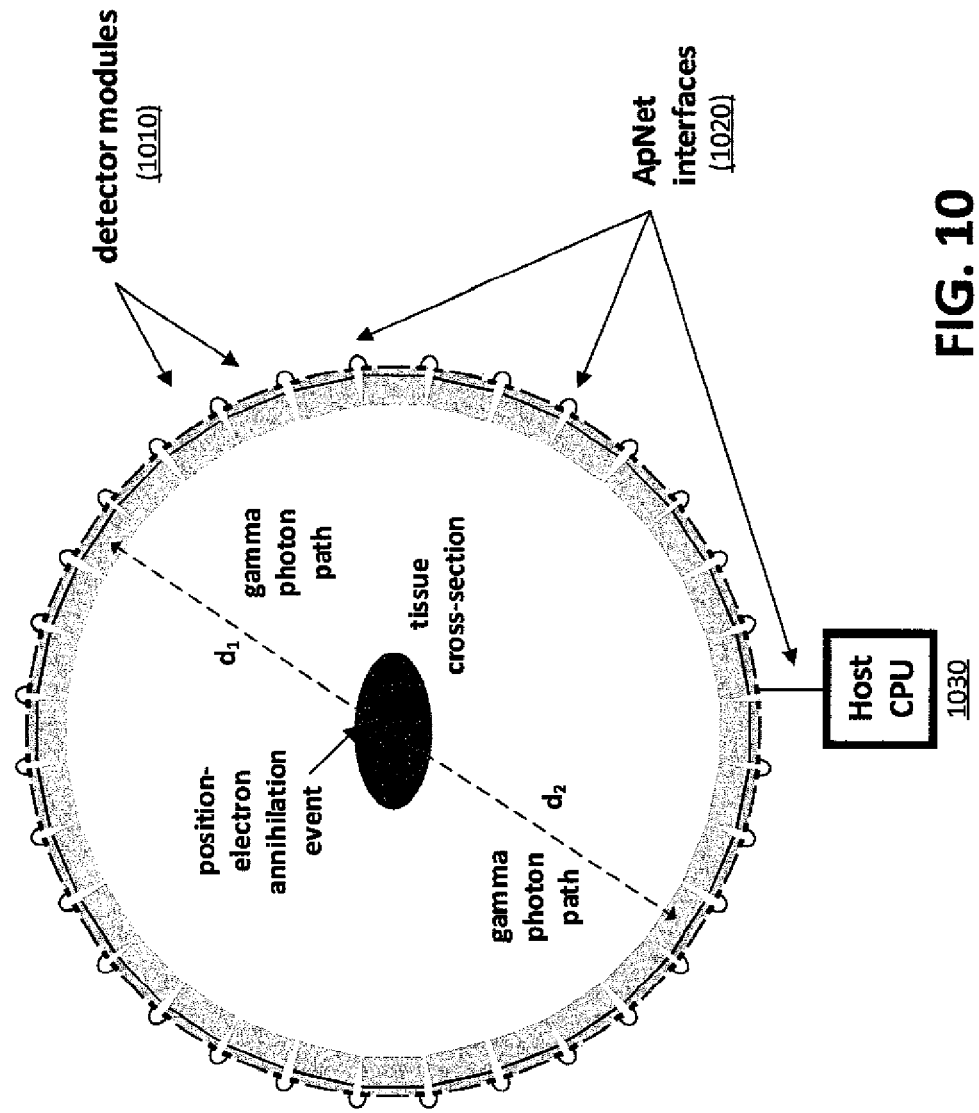
FIG. 10 illustrates one embodiment of a PET scanner based on the detector module depicted in FIG. 9.

FIG. 10 illustrates one embodiment of a PET scanner based on the detector module depicted in FIG. 9. In this embodiment, the time-synchronized network, with detector modules 1010 and ApNet interfaces 1020, is arranged in a ring configuration. The relative arrival times of gamma photons produced by a single positron-electron annihilation event allow the event to be localized relative to the two sensor modules (1010) registering hits. Multiple rings are typically used to realize a PET scanner having a cylindrical array of sensors. More rings allow more solid angle around the patient to be covered, which results in the detection of more gamma photons, in turn resulting in higher scanner sensitivity.

Each ring of sensor modules, such as a ring formed by the PET scanner cross-section 1000, is a time synchronized sensor array with each detector module (1010) connected to other detector modules and to the host CPU (1030) using ApNet (1020). The use of the AN1064, contained in the detector modules 1010, and ApNet 1020 constitute some embodiments of the inventions described herein. Their use simplifies the design of the PET scanner by combining the sensor readout and control functions with the time synchronization of the network elements. The integration of the readout electronics with the sensor network interface circuits results in lower system power dissipation, reduced component count and lower overall system cost. In addition, the use of the AN1064 (within detector modules 1010) and ApNet (1020) allow alternative scanner configurations to be realized. For example, non-cylindrical scanners may be configured to conform to the shape of the patient's body. This allows more solid angle to be covered by the scanner and leads to higher scanner sensitivity. The simplified nature of the sensor network would also allow it to be re-configurable and customizable for different patients and for scanning specific areas of the body. In addition, if the sensor modules are connected together in the manner using appropriately designed electrical cables or fiber optic cables, then the PET ring may be configured so as not to interact with the magnetic field of a magnetic resonance imaging MRI scanner. This would allow the PET scanner to be incorporated within an MM scanner.

The techniques of the invention may be used to integrate a PET scanner within a magnetic resonance imaging (MRI) scanner. The ability to overlay images taken at the same time from both MRI and PET scanners leads to better interpretation of the PET results. The problem with integrating both imaging modalities is that current PET sensor networks interfere with the operation of the MRI.

In one embodiment, the sensor modules are arranged within the MRI scanner in such a way to minimize interference with the operation of the MM scanner. This is accomplished through the proper design of the PET module ring so that its effects on the MRI are predictable and can be compensated by the MRI scanner. In some embodiments, fiber optic cables are used as the transmission paths between sensor modules.

LiDAR Systems

Figure 11:
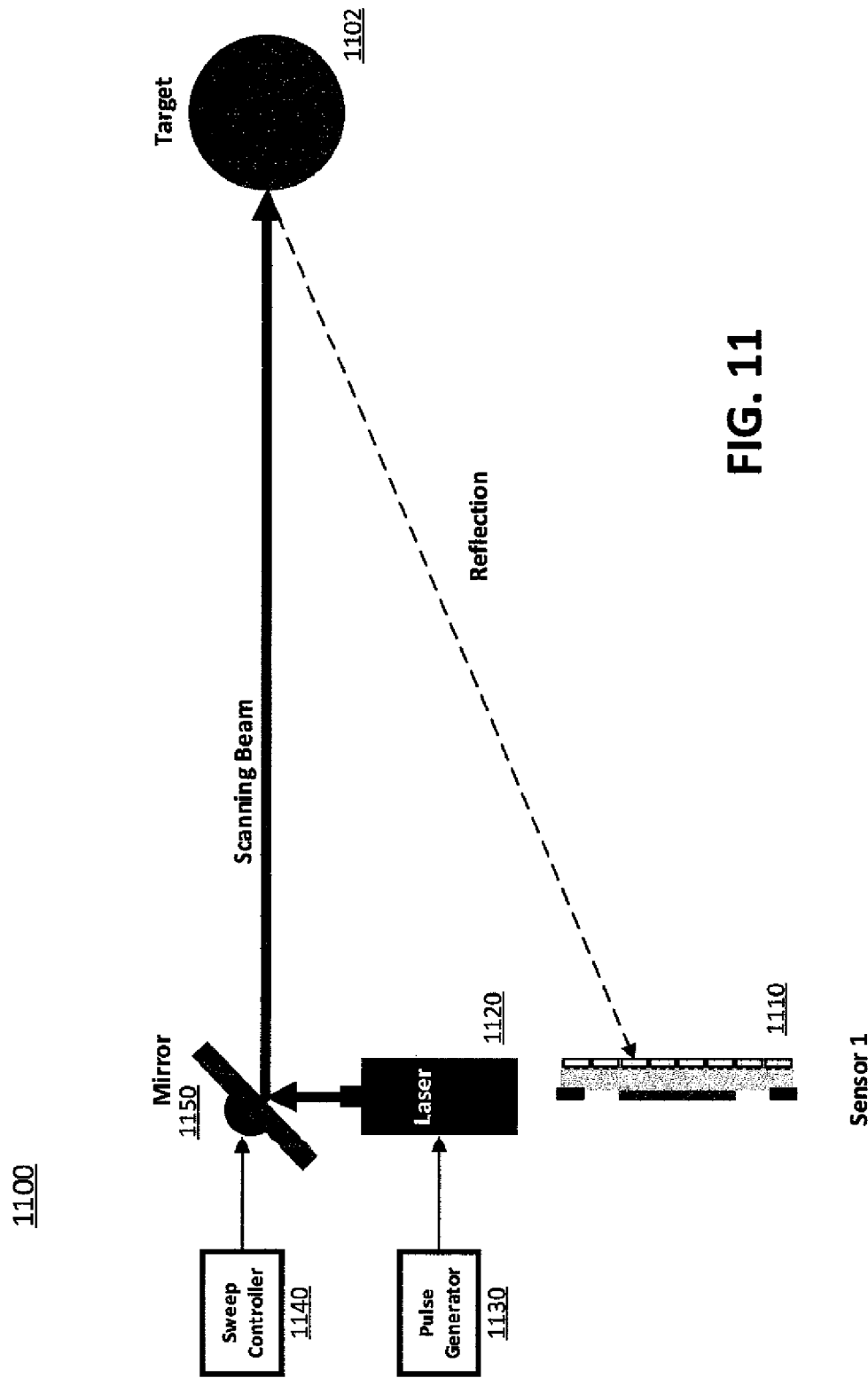
FIG. 11 illustrates one embodiment of a LiDAR system (1100) that incorporates the sensor module of the present invention.

FIG. 11 illustrates one embodiment of a LiDAR system (1100) that incorporates the sensor module of the present invention. A sensor module (1110) is used to detect light reflected from the target (1102). The laser (1120) is excited via a pulse generator (1130), and the round trip ToF of the light pulse is measured by the sensor module (1110). The time measurement allows the distance of the target (1102) to the LiDAR system (1100) to be accurately measured. As the laser beam from the laser (1120) is scanned, a three-dimensional representation of the surroundings can be created. LiDAR is presently finding widespread application in autonomous vehicles such as unmanned areal vehicles and self-driving automobiles.

When LiDAR is used for self-driving automobiles there is a possibility that LiDAR systems on different cars will interfere with each other. For example, at a traffic intersection, multiple self-driving cars may be facing each other. The LiDAR radar from one car may temporarily blind the LiDAR sensor on another car as show in LiDAR system (1200) illustrated in FIG. 12. The interfering laser (1205) may cause sensor module (1210) to register a spurious pulse and thereby produce an erroneous target distance reading.

Figure 12:
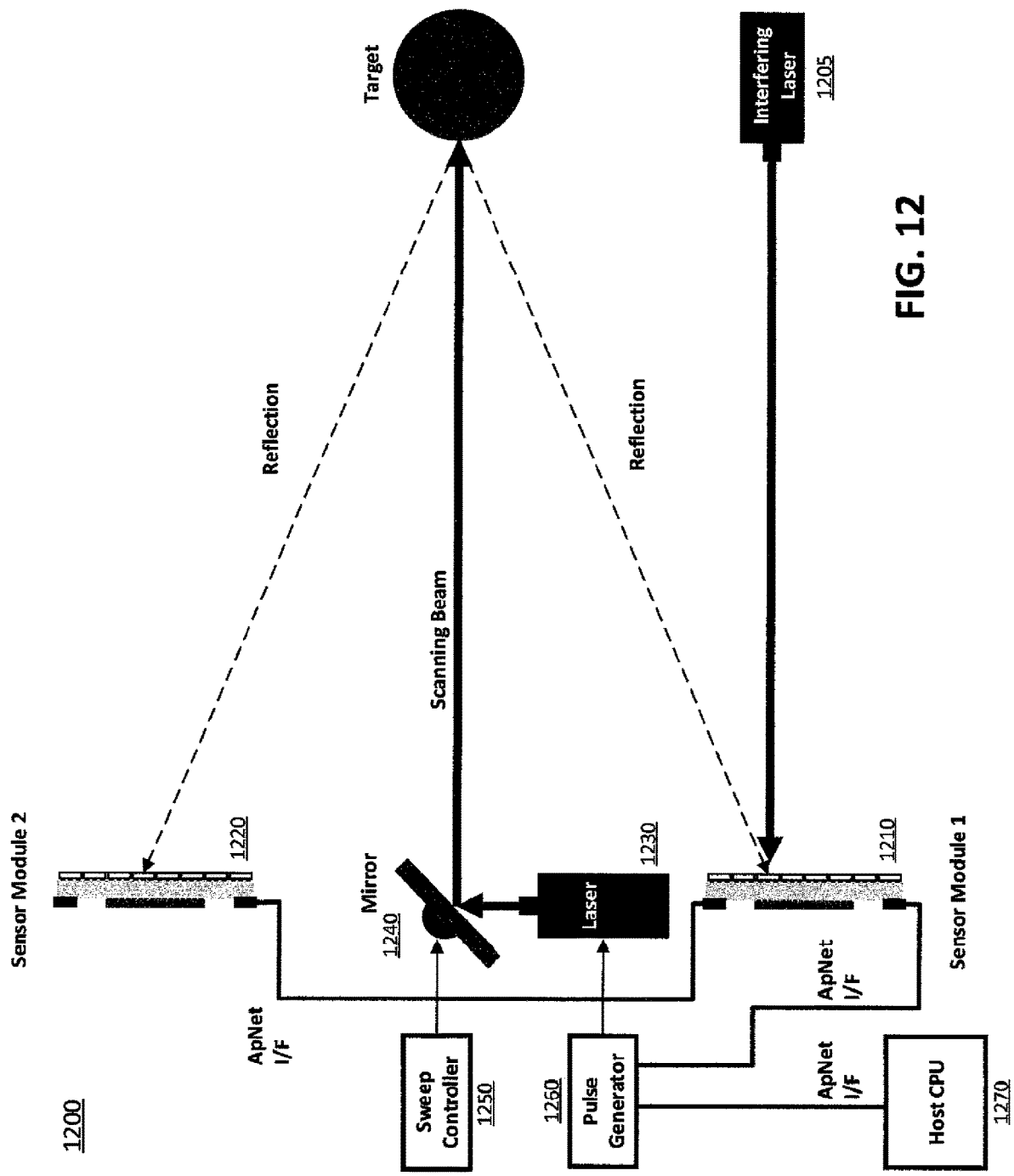
FIG. 12 illustrates the use of redundant sensors to eliminate interference effects.

FIG. 12 illustrates the use of redundant sensors to eliminate interference effects. For this embodiment, LiDAR system (1200) includes two redundant sensor modules (1210 and 1220), laser 1230, mirror 1240, sweep controller 1250, pulse generator 1260 and host CPU 1270. During normal operation, the round trip times measured by sensor module (1210) and sensor module (1220) are essentially the same. If an interfering laser (1205) corrupts the measurement made by sensor module (1210), then by sensor module (1210) and sensor module (1220) read different round trip times. Under this scenario, measurements may be rejected by the LiDAR system (1200) as spurious, and another measurement may be attempted. Furthermore, use of a third sensor module (or even more sensors) would allow spurious round trip delay measurements to be rejected in real time. The redundant sensors (sensor module 1210 and sensor module 1220) may be implemented as a time synchronized network using the invention described herein. Note that another sensor module, configured as part of the time synchronized network, may also be used to measure the laser's pulse launch time.

Flow Cytometry

Figure 13:
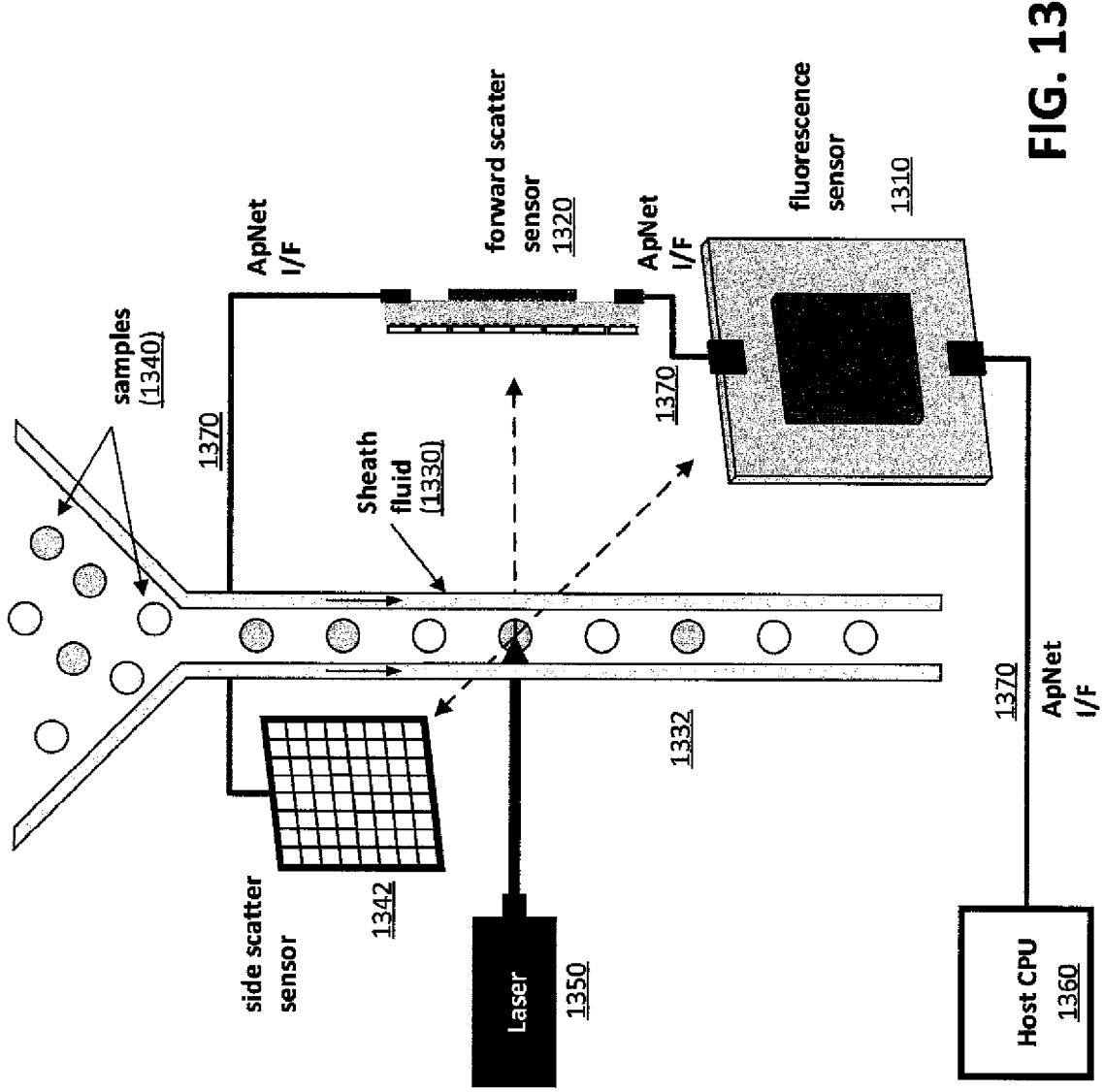
FIG. 13 illustrates one embodiment of a flow cytometry system incorporating the sensor module technology of the present invention.

Flow cytometry is a biophysical technology for performing biological assays. Applications include cell counting, cell sorting, biomarker/disease detection and drug discovery. The technique involves forcing particles through microfluidic tubes into an interaction region where the particles are illuminated by a laser beam. FIG. 13 illustrates one embodiment of a flow cytometry system incorporating the sensor module technology of the present invention. As shown in FIG. 13, biological samples (1340) are funneled through a capillary (1332) by sheath fluid (1330). The particles may be biological cells bearing fluorescent molecular tags or cytometric beads incorporating fluorophore-tagged reagents. Light scattered forward, past the particle, and light scattered to the side of the particle are measured, under the control of CPU 1360, in order to measure the size and granularity of the particles. Specifically, forward scatter data is generated from light, emanated from laser (1350), incident upon biological samples (1340) and sensed at forward scatter sensor (1320). Similarly, side scatter data is generated from light reflected off the biological sample (1340) and sensed in side scatter sensor (1342). Side scattered light is also monitored for fluorescence so as to detect the presence of fluorophore tags attached to targeted biomarkers or chemicals. For this embodiment, fluorescence data is generated from light reflected off the biological sample (1340) and sensed in fluorescence sensor (1310). The forward scatter sensor (1320), forward scatter sensor (1320), and fluorescence sensor (1310), along with the ApNet interface (1370), implement one or more embodiments of the time synchronized techniques disclosed herein.

Flow cytometers are designed to allow as many fluorophore colors as possible to be detected. Because multiple biomarkers can be targeted in a single experiment, many experiments can be carried out simultaneously (i.e. multiplexed). Each fluorophore therefore represents a measurement "channel". At present, flow cytometers can detect up to 20-30 channels. Spectral overlap in the emission of various fluorophores limits the number of channels that can be detected just by measuring fluorescence intensity. The use of fluorophores with different decay lifetimes allows a significant increase in the number of measurement channels providing that these different decay lifetimes can be detected.

Figure 14:
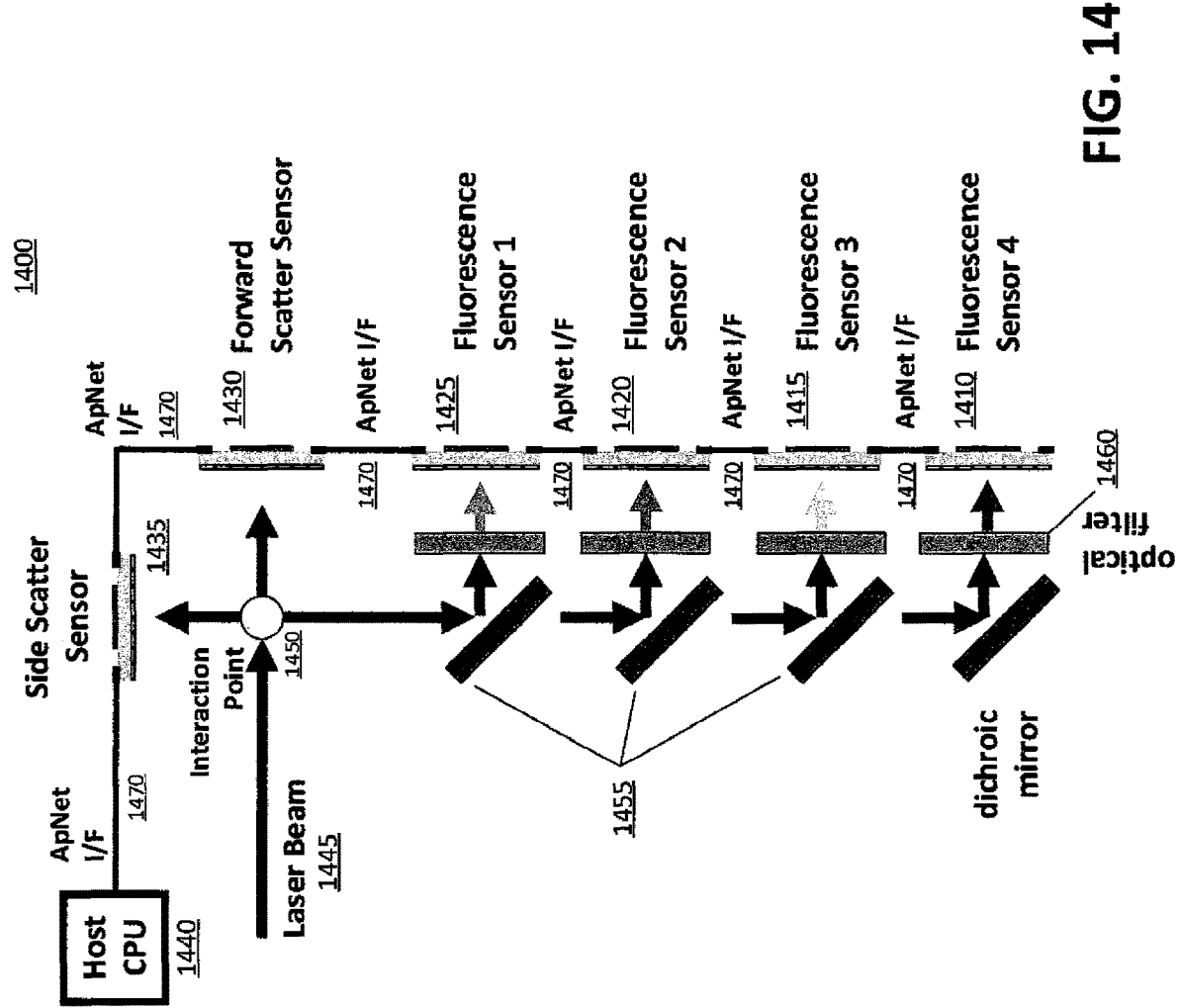
FIG. 14 illustrates a flow cytometer that allows for decay lifetime measurement.

FIG. 14 illustrates a flow cytometer that allows for decay lifetime measurement. The sensor network in FIG. 14 allows the relative signal arrival time at fluorescence sensors (1425, 1420, 1415 and 1410) to be measured relative to the signal arrival time at side scatter sensor (1435). Specifically, under control of host CPU (1440), laser beam 1445 strikes biological samples, at interaction point (1450), and reflects onto side scatter sensor (1435), forward scatter sensor (1430), as well as dichroic mirrors (1455). The reflection, onto the dichroic mirrors (1455) is filtered through optical filter (1460) and then projected onto the fluorescence sensors (1425, 1420, 1415 and 1410). Each sensor module (1425, 1420, 1415, 1410, 1430 and 1435) includes a TDU that allows the arrival time of the light from the interaction point to be logged. The arrival times at the fluorescence sensors (1425, 1420, 1415 and 1410) relative to the side scatter sensor (1435) is a measure of the fluorescence decays times. The sensor synchronization (to picosecond accuracy) is achieved, via the principles disclosed herein, by using ApNet (1470) to connect the sensor modules (1425, 1420, 1415, 1410, 1430 and 1435) to each other.

Confocal Microscopy

Confocal microscopes allow samples to be scanned using a laser beam, which excites fluorophore in a minute volume at the focal point of the laser beam. The fluorophores are attached to molecules of interest. The light emitted by the fluorophores is sensed using a sensor array to detect the presence of specific molecules. By recording the fluorescence measurements at each laser focal point location as the laser is scanned, a two or three-dimensional representation of the sample can be produced.

In some applications the intensity of the measured fluorescence in a specific wavelength range is the quantity of interest. In FLIM applications, it is the decay lifetime of the fluorescence (within a specific wavelength range) that is of interest. FLIM allows more fluorophore tags (i.e. measurement channels) to be used just as in flow cytometry as described above. In addition, FLIM allows the measurement of FRET, which allows an indirect measurement of the physical distance between molecules of interest within the cell or cytometric bead.

In FLIM applications, the emission rate of photons may be so low such that, in response to a laser pulse, only one or a few photons is detected by the sensor array. The decay lifetime is measured by repeatedly pulsing the sampling laser beam and logging the photon arrival times (relative to the laser pulse time). Doing this over thousands of pulses allows a histogram to be created that directly indicates the fluorescence decay time.

Because each laser pulse creates so few photons it is desirable to have many sensors positioned around the sample in order to cover as much solid angle as possible which maximizes photon collection efficiency and, therefore, microscope sensitivity. For these sensors to all be able to log photon arrival times from the same laser pulse the sensors need to be time synchronized to picosecond accuracy. Using the principles described in this invention the sensors can be implemented using an array of sensors connected via ApNet.

What is claimed is:

1. A positron emission tomography (PET) system, comprising:
    a plurality of detector modules comprising:
        a detector unit to receive a plurality of positrons and electrons emitted from a positron-electron annihilation event in a radioactive dye within a chemically active region located within a subject and to convert the gamma rays produced by the positron-electron annihilation event;
        a plurality of a readout circuits, coupled to the detector unit, to record the positron-electron annihilation event for the detector module;
    a plurality of time digitizer units (TDUs), at least one for each of the readout circuits, to generate at least one timestamp to record a time of the positron-electron annihilation event;
    a time synchronized network comprising a succession of a plurality of master integrated circuits ("ICs") and a plurality of slave ICs configured in adjacent detector modules, to perform synchronization of timing between adjacent detector modules;
        a synchronizing circuit on the slave IC for receiving a global offset, comprising global timing information and a delay, $T_{latency}$, between the master IC and the slave IC, the synchronizing circuit comprising;
            at least one phase lock loop on the slave IC to generate timing signals;
            the time digitizer unit (TDU), comprising plurality of gates, to receive the timing signals and to generate a timestamp within a 50 picosecond delay from one of the gates, to form the least significant bit (LSB) of the time stamping circuit;
            at least one adder for adding the global offset to the LSBs of the timestamp to generate the timestamp for the event;

at least one processing unit to receive the synchronized timestamps and to localize the events relative to two of the detector modules that recorded the positron-electron annihilation event.

2. The positron emission tomography (PET) system as set forth in claim 1, within the detector modules comprise:
   a plurality of scintillator crystals to convert the gamma rays, produced by the positron-electron annihilation event, into visible light; and
   a plurality of SiPMT devices, coupled to the scintillator crystals, to read the visible light.

3. The positron emission tomography (PET) system as set forth in claim 2, wherein the detector modules comprise the time synchronized network implemented on an integrated circuit combined with the SiPMT devices on a printed circuit board (PCB) module.

4. The positron emission tomography (PET) system as set forth in claim 1, within the detector modules are configured in a ring.

5. The positron emission tomography (PET) system as set forth in claim 4, further comprising a plurality of the rings, arranged cylindrically, to form a cylindrical array of detector modules.

6. The positron emission tomography (PET) system as set forth in claim 4, wherein each of the rings comprises one of the time synchronized networks.

7. The positron emission tomography (PET) system as set forth in claim 1, wherein the detector modules are arranged to conform to the shape of a patient's body.

8. The positron emission tomography (PET) system as set forth in claim 1, wherein the detector modules are arranged so as to be re-configurable and customizable for different patients and for scanning specific areas of the body.

9. The positron emission tomography (PET) system as set forth in claim 1, wherein the detector modules are arranged within an MM scanner in such a way that they minimize interference with the operation of the MM scanner.

10. The positron emission tomography (PET) system as set forth in claim 1, wherein the slave IC comprises a synchronization block to allow a loopback delay to be measured and conveyed to the master IC between adjacent detector modules.

11. The positron emission tomography (PET) system as set forth in claim 10, wherein the synchronization block comprises a delay loop comprising at least one transmission path between the master IC and the slave IC, the synchronization block to propagate a signal through the transmission path, during an initialization, and to calculate the $T_{latency}$, between the master IC and the slave IC.

12. The positron emission tomography (PET) system as set forth in claim 1, wherein the synchronizing circuit on the slave IC for synchronizing timing of the master IC to timing of the slave IC, further comprises:
   the time digitizer unit (TDU) for receiving a global offset, comprising global timing information and timing delay information between the master IC and the slave IC ($T_{latency}$), and for generating a timestamp, synchronized to the timing of the master IC, in response to the positron-electron annihilation event, the TDU comprising:
      a counter for generating a count; and
      at least one adder for adding the global offset, the count to and the LSBs of the timestamp to generate the timestamp for the event.

13. The positron emission tomography (PET) system as set forth in claim 1, further comprising a network protocol for connecting the detector modules together.

* * * * *